US005646260A

United States Patent [19]
Letsinger et al.

[11] Patent Number: 5,646,260
[45] Date of Patent: Jul. 8, 1997

[54] OLIGONUCLEOTIDES HAVING MODIFIED INTERNUCLEOSIDE LINKAGES

[76] Inventors: Robert L. Letsinger, 316 3rd St., Wilmette, Ill. 60091; Sergei M. Gryaznov, 2 Clark Dr., San Mateo, Calif. 94401

[21] Appl. No.: 471,248

[22] Filed: Jun. 6, 1995

Related U.S. Application Data

[62] Division of Ser. No. 376,291, Jan. 23, 1995, Pat. No. 5,476,295, which is a continuation of Ser. No. 12,050, Feb. 1, 1993, abandoned.

[51] Int. Cl.$^6$ ................................................. C07H 21/00
[52] U.S. Cl. ...................... 536/23.1; 536/24.3; 536/24.5
[58] Field of Search ................................ 536/23.1, 24.3, 536/24.5

[56] References Cited

U.S. PATENT DOCUMENTS

| | | | |
|---|---|---|---|
| 4,959,463 | 9/1990 | Froehler et al. | 536/25.34 |
| 5,185,444 | 2/1993 | Summerton et al. | 544/81 |
| 5,235,033 | 8/1993 | Summerton et al. | 528/391 |
| 5,264,566 | 11/1993 | Froehler et al. | 536/25.34 |

FOREIGN PATENT DOCUMENTS 0490281  6/1992  European Pat. Off. .

OTHER PUBLICATIONS

Mag et al.(I), "Synthesis and Selective Cleavage of an Oligodeoxynucleotide Containing a Bridged Non–Chiral Internucleotide 3'–Phosphoramidate Linkage," *Tett. Lett.*, 33(48), 7319–7322 (1992).

Kiedrowski et al., "Parabolic Growth of a Self–Replicating Hexadeoxynucleotide Bearing a 3',5'–Phosphoramidate Linkage," *Angew. Chem. Intl. Ed.*, 30(4), 423–426.

Mag et al.(II), "Synthesis and Selective Cleavage of Oligodeoxyribonucleotides Containing Non–chiral Internucleotide Phosphoramidate Linkages," *Nucleic Acids Res.*, 17(15), 5973–5988 (1989).

Gryaznov et al.(I), "Synthesis of Oligodeoxyribonucleotides Containing Phosphoramidate Internucleotide Bonds with the Use of the Atherton–Todd Reaction," *Bioorg. Khim.*, 15(7), 994–996 (1989); *Chem. Abstr.*, 112(11), p. 807, Abstr. No. 99092x (1990).

Azhayev et al.(I), "Synthesis of Phosphoramidate Analogues of Short Oligonucleotides," *Nucleic Acids Research Symposium Series*, No. 9, IRL Press, Ltd., London, UK, 1981, pp. 251–254.

Krayevsky et al., "Synthesis of Oligonucleotides with 5'→3' Phosphoamidoester Bonds," *Nucleic Acids Research Symposium Series*, No. 9, IRL Press, Ltd., London, UK, 1981, pp. 203–205.

Shabarova et al., "Chemical Development in the Design of Oligonucleotide Probes for Binding to DNA and RNA," *Biochemie*, 70, 1323–1334 (1988).

Gromova et al., "Interaction of EcoRII Restriction and Modification Enzymes with Synthetic Fragments of DNA. IV. DNA Duplexes with Phosphoramide and Pyrophosphate Internucleotide Bonds—Substrates for the Study of Single–Strand Breaks," *Molekulyarnaya Biol.*, 201), 29–40 (1986) (translation into English, Plenum Press, 1986).

Zaitseva et al., "Aminonucleosides and their Derivatives. X. 2'–Deoxydinucleoside Phosphates and 2'–Deoxydinucleotides with Phosphoramide Bonds," *Bioorg. Khim.*, 10(3), 410–407 (1984) (in Russian with English Abstract following).

Lohrmann et al., "Template–directed Synthesis of High Molecular Weight Polynucleotide Analogues," *Nature*, 261, 342–344 (1976).

Gibbs et al., "The Synthesis of Phosphoramidates from Silylphosphites and Azides," *Tett. Lett.*, 1977(8), 679–682.

Azhayev et al.(II), "Synthesis of Phosphoramidate Analogs of Ribonucleoside Phosphates," *Coll. Czech. Chem. Comm.*, 44, 792–798 (1979).

Mungall et al., "Use of Phosphorus Oxychloride in Synthesizing Nucleotides and Oligonucleotides," *Nucleic Acids Research*, 1(4), 615–627(1974).

Greene et al., "Formation of Internucleotide 3'–5' Phosphoramidate Links by Direct Coupling of Phosphoryl and Amino Groups," *Nucleic Acids Research*, 2(7), 1123–1127 (1975).

Azhayev et al.(III), "Aminonucleosides and Their Derivatives. IX. Synthesis of Short Oligoribonucleotides with Phosphoramide Internucleotide Links," *Bioorg. Khim.*, 8(9), 1218–1224 (1982); *Chem. Abstr.*, 98(5), p. 679, Abstr. No. 34893g (1983).

Sokolova et al.(I), "A New Method for Synthesis of Oligodeoxyribonucleotides with Phosphoramide Internucleotide Bond," *Bioorg. Khim.*, 10(1), 75–78 (1984); *Chem. Abstr.*, 100(25), p. 646, Abstr. No. 210339b (1984).

Isagulyants et al., "Template–Directed Condensation of Oligodeoxyribonucleotide Phosphorimidazolides—The General Way of Synthesis of Natural and Modified DNA—Duplexes,"*Bioorg. Khim.*, 11(2), 239–247 (1985); *Chem. Abstr.*, 104(1), p. 567, Abstr. No. 6130e (1987).

Gryaznov et al.(II), "The Use of the Atherton–Todd Reaction for Synthesis of Oligodeoxyribonucleotides with Phosphorus Amide Internucleotide Bonds," *Vestn. Mosk. Univ., Ser. 2:Khim.*, 27(4), 421–424 (1986); *Chem. Abstr.*, 108(5), p. 680, Abstr. No. 38263z (1988).

Letsinger et al.(I), "Enzymatic Synthesis of Polydeoxyribonucleotides Possessing Internucleotide Phosphoramidate Bonds," *J. Am. Chem. Soc.*, 94, 292–293 (1972).

Letsinger et al.(II), "Phosphoramidate Analogs of Oligonucleotides," *J. Org. Chem.*, 35(11), 3800–3803 (1970).

(List continued on next page.)

*Primary Examiner*—John Kight
*Assistant Examiner*—L. Eric Crane

[57]  ABSTRACT

Novel oligonucleotides, method for improving the hybridization properties of oligonucleotides and novel processes for preparing 3'–phosphorylated oligonucleotides are disclosed.

1 Claim, No Drawings

OTHER PUBLICATIONS

Mungall et al., "Use of the Azido Group in the Synthesis of 5' Terminal Aminodeoxythymidine Oligonucleotides," *J. Org. Chem.*, 40(11), 1659–1662 (1975).

Zielinski et al.(I), "Oligomerization of Activated Derivatives of 3'-Amino-3'-deoxyguanosine on Poly(C) and Poly(dC) Templates," *Nucleic Acids Research*, 13(7), 2469–2484 (1985).

Zielinski et al.(II), "Oligoaminonucleoside Phosphoramidates. Oligomerization of Dimers of 3'-Amino-3'-deoxynucleotides (GC and CG) in Aqueous Solution," *Nucleic Acids Research*, 15(4), 1699–1715 (1987).

Zielinski et al.(III), "Autocatalytic Synthesis of a Tetranucleotide Analogue," *Nature*, 327, 346–347 1987).

Bannwarth, "166. Solid-Phase Synthesis of Oligodeoxynucleotides Containing Phosphoramidate Internucleotide Linkages and Their Specific Chemical Cleavage," *Helv. Chim. Acta*, 71, 1517–1527 (1988).

Sproat et al., "The Synthesis of Protected 5'-Amino-2', 5'-dideoxyribonucleosides-3'—O-phosphoramidites; Applications of 5'-Amino-oligodeoxyribonucleotides," *Nucleic Acid Research*, 15(5), 6181–6196 (1987).

Letsinger et al. (III), "Incorporation of 5'-Amino-5'-deoxythymidine 5'-Phosphate in Polynucleotides by Use of DNA Polymerase I and a φX174 DNA Template," *Biochemistry*, 15(13), 2810–2816 (1976).

Letsinger et al., "Enzymatic Synthesis of Duplex Circular φX174 DNA Containing Phosphoramidate Bonds in the (–) Strand," *Nucleic Acids Research*, 3(4), 1053–1063 (1976).

Gryaznov et al.(III), "A New Method for the Synthesis of Oligodeoxyribonucleotides Containing Internucleotide Phosphoramidate Bonds," *Tetrahedron Letters*, 31(22), 3205–3208 (1990).

Barone et al., "In situ Activation of Bis-dialkylaminophosphines—A New Method for Synthesizing Deoxyoligonucleotides on Polymer Supports," *Nucleic Acids Research*, 12(10), 4051–4061 (1984).

Agrawal et al., "Oligodeoxynucleoside Phosphoramidates and Phosphorothioates as Inhibitors of Human Immunodeficiency Virus," *Proc. Nat. Acad. Sci. USA*, 85, 7079–7083 (1988).

Froehler et al., "Nucleoside H-Phosphonates: Valuable Intermediates in the Synthesis of Deoxyoligonucleotides," *Tetrahedron Letters*, 27(4), 469–472 (1986).

Miller et al., "Synthesis of Oligo-2'-deoxyribonucleoside Methylphosphonates," Ch. 6 in *Oligonucleotides and Analogues: A Practical Approach*, Eckstein (ed.), Oxford University Press, London, UK, 1991, pp. 137–154.

Alul et la., "Oxalyl-CPG: A Labile Support for Synthesis of Sensitive Oligonucleotide Derivatives," *Nucleic Acids Research*, 19(7), 1527–1532 (1991).

Sokolova et al.(II), "Chemical Reactions with DNA Duplexes. Cyanogen Bromide as an Effective Oligodeoxyrobonucleotide Coupling Agent," *FEBS Letters*, 232(1), 153–155 (1988).

Dolinnaya et al., "Site-Directd Modification of DNA Duplexes by Chemical Ligation," *Nucleic Acids Research*, 16(9), 3721–3738 (1988).

Zon, "Oligonucleotide Analogues as Potential Chemotherapeutic Agents," *Pharmaceutical Research*, 5(9), 539–549 (1988).

OLIGONUCLEOTIDES HAVING MODIFIED INTERNUCLEOSIDE LINKAGES

This application is a divisional of U.S. Ser. No. 08/376,291, filed Jan. 23, 1995, now U.S. Pat. No. 5,476,925, issued Dec. 19, 1995, which is a continuation of U.S. Ser. No. 08/012,050 filed Feb. 1, 1993, now abandoned.

GRANT REFERENCE

The research carried out in connection with this invention was supported in part by a grant from the NIH (GM10265).

TECHNICAL FIELD

The present invention relates to oligonucleotides having use in diagnostics and antisense research and therapeutics.

BACKGROUND OF THE INVENTION

Modified oligonucleotides derived in part from 5'- or 3'-aminonucleosides have potential as tools in diagnostics and antisense research. This potential rests on both the differences and similarities in properties of the modified and natural oligomers. Thus, it has been shown that the highly nucleophilic amino groups of oligomers with terminal aminonucleosides serve as reactive sites for chemical attachment of nucleotide units,[1-7] oligonucleotides,[8-11] and reporter groups[12], and that a terminal 5'-amino group inhibits enzymatic hydrolysis.[1] Oligomers with one or more internucleoside anionic 3'P-5'N phosphoramidate links [—OP(O)(O⁻)NH—] have been prepared by stepwise coupling to aminooligonucleotides,[1-6] condensation with dimer blocks,[16] chemical ligation on templates, 8-11 and enzymatic synthesis utilizing aminonucleoside triphosphates, templates and primers.[13-15] Chemical ligation[8-11] and polymerization[4-6] have also been used to generate internucleoside 3'N-5'P phosphoramidate links. The anionic phosphoramidate derivatives resemble natural oligonucleotides in serving as primers for chain extension by DNA polymerase[14,15]; however they differ in hydrolytic stability in that the P-N bonds are unusually sensitive to aqueous acids[1,7,15] and are unusually resistant to some restriction enzymes.[9-11]

The present invention provides novel oligonucleotides having modified internucleoside links and having terminal 3'-amino groups.

SUMMARY OF INVENTION

The present invention provides novel oligonucleotides having from 10 to 30 bases and having at least one internucleoside link selected from:

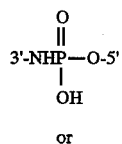  (I)

or

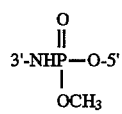  (II)

wherein each linkage is depicted in the 3'→5' orientation. The novel oligonucleotides can have up to 29 internucleoside links selected from those depicted above, but more typically the oligonucleotide will have from 1 to 4 internucleoside links selected from those depicted above with the remaining internucleoside links being phosphodiester links.

The present invention also provides novel oligonucleotides having from 10 to 30 bases and having a terminal 3'-amino group. The 3'-amino-oligonucleotides have either phosphodiester internucleoside links or internucleoside links selected from I or II or:

  (III)

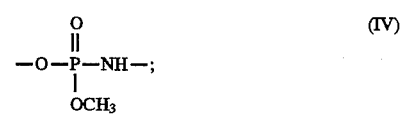  (IV)

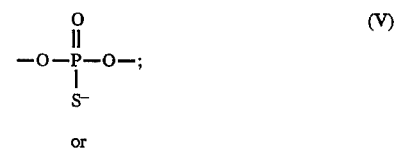  (V)

or

  (VI)

wherein each linkage is depicted in the 5'→3' orientation. The 3'-amino-oligonucleotides can have up to 19 internucleoside links selected from I to VI. More typically when the internucleoside link is selected from I to V, the oligonucleotides will have from 1 to 4 such internucleoside links. Internucleoside links other than those depicted by I to VI in the 3'-amino-oligonucleotide of the present invention are comprised of phosphodiester links.

The present invention also provides a method for improving the hybridization properties of an oligonucleotide which comprises incorporating internucleoside links selected from I to VI above into said oligonucleotide. Another aspect of the present invention is the incorporation of a 3'-amino group into an oligonucleotide to improve its hybridization properties. The present invention further provides a new process for synthesizing oligonucleotides on a solid support.

DETAILED DESCRIPTION OF INVENTION

The oligonucleotides of the present invention are oligodeoxyribonucleotides and oligoribonucleotides. The internucleoside links of the oligonucleotides of the present invention can be depicted as follows wherein B represents the base cytosine, guanine, adenine, thymine and A represents hydrogen in the case of an oligodeoxyribonucleotide or B represents adenine, uracil, cytosine or guanine and A represents hydroxyl in the case of an oligoribonucleotide:

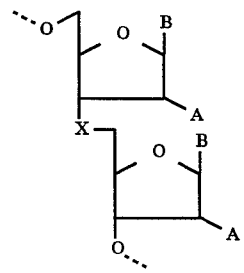

wherein X— represents:

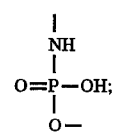

(I)

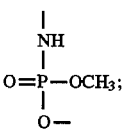

(II)

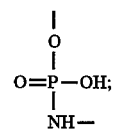

(III)

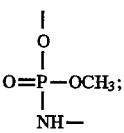

(IV)

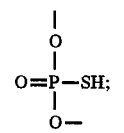

(V)

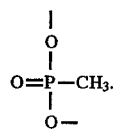

(VI)

The oligonucleotides of the present invention contain internucleoside links selected from groups I or II when the oligonucleotide has a terminal 3'-OH group. The oligonucleotides of the present invention having a 3'-amino terminal group have internucleoside links selected from I to VI.

It is contemplated that the oligonucleotides of the present invention can have from 1 to 19 internucleoside links selected from one of groups I to VI with any internucleoside links other than said link from I to VI being a phosphodiester group except that the terminal 3'-amino-oligonucleotides can have from 1 to 19 phosphodiester internucleoside links.

Experimental examples of compounds representative of the present invention are depicted in Tables 1 and 2 below. These compounds are thymidine oligonucleotides with internucleoside anionic phosphoramidate links, i.e.,

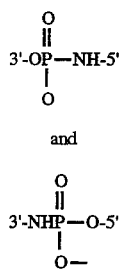

abbreviated herein as pn and np, respectively, or with internucleoside uncharged phosphoramidate links, i.e.

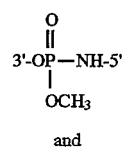

and

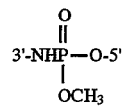

abbreviated herein as p(OMe)n and n(O Me)p, respectively, and compounds with terminal amino groups. These compounds were prepared on long-chain amino alkyl controlled pore glass (LCAA CPG) supports using a commercial thymidine cyanoethyl phosphoramidite reagent for synthesis of the conventional portions and appropriate dimer blocks and aminonucleoside derivatives for the modified sections. Alternatively, other solid supports such as polystyrene can be used.

The 3'O-P(O)(O⁻)NH-5'phosphoramidate links in compounds 1–5 were introduced by block coupling of dimer I and II as generally described by S. Gryaznov et al.[16], except that the intermediate —P(O)(OCH$_3$)NH— units in the chain were deprotected with ammonium hydroxide (16 hours, 55° C.) rather than thiophenoxide. The couplings proceeded well (~97% for the dimer block) and afforded good quality oligomers. The HPLC profiles for compound 3 and the products obtained by mild acid treatment showed that compounds could be selectively cleaved at the middle internucleoside link under mildly acidic conditions. The experiment demonstrated that compound 3 indeed has a centrally positioned phosphoramidate link.

The chemistry employed in generating the 3'-terminal "Tp(ome)nT" unit in compounds 11–13 (Table 1) is outlined in Scheme 1 (Chart B). 5'-Monomethoxytritylamino-5'-deoxythymidine was loaded onto an oxalyl-CPG support. Following acidic deprotection, the anchored aminonucleoside (II) was condensed with a thymidine methyl phosphoramidite reagent to give a support bound dimer unit (III). Mild treatment with ammonium hydroxide liberated the dimer (IV), which was identical in properties to a sample prepared in solution as described below. The methyl phosphoramidate link was found to be relatively resistant to ammonium hydroxide. Only ~7% of dimer V was degraded on exposure to concentrated ammonium hydroxide at 55° C. for 1 hour, whereas all of a sample of the corresponding methyl triester [—OP(O)(OCH$_3$)O— internucleoside link] was cleaved under the same conditions. This stability enables the methyl ester phosphoramidate derivatives to be recovered intact from the solid support under moderately basic conditions. The group is sufficiently robust that an oligomer containing this modification and joined to the support by a succinyl anchor can be liberated with little loss of the methyl ester group.

The support bound dimer, III, served as the starting unit for synthesis of oligomers 11–13. A thymidine H-phosphonate reagent was used to introduce monomer units and I was used to introduce "Tp(ome)nT" blocks. Cleavage from the support with ammonium hydroxide (55°, 20 min) afforded the desired methyl ester phosphoramidate derivatives. With more vigorous cleavage conditions (ammonium hydroxide, 55°, 16 hours) the demethylated products (6–8) were obtained. RP HPLC profiles for one set of related oligomers (11,6) indicated the stereoisomers for the methyl ester (11) appear as two peaks in the reversed phase chromatogram. The corresponding anionic amidate (6) elutes more rapidly and as a single peak.

Similar chemistry based on 3'-aminodeoxythymidine was developed for the synthesis of oligonucleotides containing 3'-NHP(0)(O⁻)0–5 and 3'-NHP(0)(OCH₃)0–5' internucleoside links (6–8, 11–13). The route to the dimer block (X) used to introduce these links is indicated in Scheme 2 (Chart C). 3'O-Levulinylthymidine (VIa) was converted to a hydrogen phosphonate diester (VIIa), which was oxidatively coupled (P. Atherton et al., J. Chem Soc., 1945, 269) to 5'O-trityl-3'amino-3'deoxythymidine. Treatment of the resulting dimer (VIIIa) with hydrazine, followed by conventional phosphitilation,[18] gave the desired phosphoramidite synthon (X) (see Chart A). In agreement with the structure, the $^{31}$p NMR spectrum showed four peaks (R,S stereoisomers at each phosphorus atom). This block functioned well as a phosphitilating agent in the synthesis of oligomers 14,15, with coupling yields averaging ~97%. Some pertinent chemical properties of the internucleoside 3'N-5'P phosphoramidate link are also indicated in Scheme 2 (Chart C). Dimer IX can be hydrolyzed efficiently in steps through intermediates XI and XII to 3'-aminodeoxythymidine and thymidine 5'-phosphate by successive treatment with 0.8% trifluoroacetic acid in dichloromethane, concentrated ammonium hydroxide, and aqueous 80% acetic acid.

Acidic cleavage of oligomers with the internucleoside "TnpT" link affords oligonucleotides terminated with a 3'-amino group. As a more direct route to such compounds, Scheme 2 (Chart C) was modified by starting with a conventional thymidine-succinyl-cpg support (VIb) in place of 3'-levulinylthymidine, and converting it to the dimer derivative, (VIIIb.) That the reactions proceeded properly on the solid support was demonstrated by partially deprotecting (80% aqueous acetic acid) and freeing the dimer (ammonium hydroxide), which proved identical to the sample of (XI) prepared in solution from (VIa) as described below. Oligomer 18 was obtained by extending the chain from (VIIIb), cleaving the succinyl anchor and the methyl ester by concentrated ammonium hydroxide, and hydrolyzing the phosphoramidate link in the resulting eleven-mer, TTTTTTTTTTTnpT. Chromatograms for the eleven-mer and its hydrolytic products were consistent with the structures. Analogous chemistry was employed in synthesizing the methyl phosphonates, except a β-cyanoethyl derivative (VIIIc) was used in place of a methyl phosphotriester derivative (VIIIb) so that mild conditions could be used in the final deprotection step.

The aminothymidine units at the 5' end of oligomers 17 and 19 were incorporated in the oligomer via a cyanoethyl phosphoramidite reagent by the procedure of W. Bannwarth[7].

Both the 3' and 5' amino groups in the oligonucleotides are readily available for derivatization, as shown by efficient conversion of 17 and 19 to the mono- and di-fluorescein derivatives, respectively, by treatment with excess fluorescein isothiocyanate. It has been reported that a terminal 5' amino group hinders hydrolysis of an oligonucleotide by the exonuclease, spleen phosphodiesterase, which hydrolyzes oligonucleotides in a stepwise fashion from the 5'end[1]. As a complement, we find that the 3' terminal amino group in 18 retards hydrolysis by snake venom phosphodiesterase, an exonuclease that works from the 3' end of the oligomer. Under conditions where TTTTTTTTTT was completely degraded to thymidine by snake venom phosphodiesterase and alkaline phosphatase within 3 hours, only about 30% of 18 was attacked. However, on incubation overnight at 37° C., 18 hydrolyzed completely to thymidine and 3'-amino 3'-deoxythymidine.

Oligonucleoside phosphoramidates and phosphorothioates having a 3'-amino and internucleoside links selected from (V) and (VI) depicted above are prepared as generally described herein and by S. Agrawal et al.[19] S. Gryaznov et al.[16] disclosed oligodeoxyribonucleotides containing internucleotide phosphoramidate bonds.

The oligonucleotides of the present invention, but terminated with a 3'-phosphoryl group can be synthesized using a solid support having a linker, such as a long chain alkyl having a terminal amino group thereon. The solid support and an activated nucleoside β-cyanoethyl-N,N-diisopropylphosphoramidate of the formula:

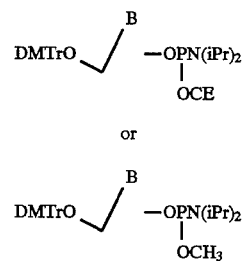

wherein B is a nucleoside selected from adenine, cytosine, thymine, guanine or uracil, appropriately protected by means known in the art; DMTr is dimethoxytrityl, or other suitable protecting group; and CE is cyanoethyl. The resulting immobilized phophoramidite is oxidized to give a diester phosphoramidate linkage, i.e.

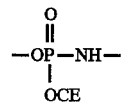

between the solid support and the nucleoside; then the product is detritylated by treatment with mild acid, e.g., dicloroacetic acid in dichloromethane to generate a 5'-hydroxy group for further coupling, i.e. reaction with an activated nucleoside having a 3'-phosphorus containing group capable of reacting with the 5'-hydroxy group. The deprotecting and coupling are continued until the desired oligonucleotide is obtained. The oligonucleotide is removed from the solid support by treatment with (a) ammonium hydroxide to remove base protecting groups and P-O protecting groups and (b) by acid hydrolysis using, e.g., acetic acid. This procedure is exemplified as follows: LCAA controlled pore glass (50 mg., ~3.5 μmole amino groups, 500 Å, Sigma was treated with (a) DMT-T β-cyanoethyl N,N-diisopropl-phosphoramidite reagent (0.1M in acetonitrile) and tetrazole (0.4M; 3 min reaction time) followed by (b) iodine (0.15M in pyridine/THF/H₂O, 10/10/1, v/v/v, 1 min). The loading amounted to ~64 μmole of nucleoside/g of support, as judged by the dimethoxytrityl test. Work-up gave 27 A₂₆₀ units of nucleotide material (3.1 μmole calculated as thymidine units), which was found by HPLC analysis to be primarily 3'-thymidylic acid (~97%). Work-up comprised the steps of: treatment with ammonium hydroxide (55° C., 2 hours for thymine or up to 16 hours for protected bases), concentration to dryness, exposure to 80% aq. acetic acid (4 hours), filtration, and concentration of the filtrate. Small amounts of thymidine (~2%) and cyclic thymidine monophosphate (~1%), probably formed by hydrolyric cleavage at the 3'-O-P bond and by substitution at the phosphorus atom by the 5'-hydroxyl group, were observed as minor by-products. Hydrolysis of the thymidylic acid to thymidine by alkaline phosphatase confirmed the presence of the phosphoryl group.

A dimer, (Tp)$_2$, and a decamer, (Tp)$_{10}$, were then synthesized by this route. The coupling yields based on the dimethoxytrityl cation test (98–99%) indicated that the anchor held fast throughout the synthetic sequence. Presence of a terminal phosphoryl group in the ten-mer was demonstrated by the $^{31}$P NMR spectrum (DO$_2$)δ=0.25 ppm for phosphoryl, –0.69 ppm for phosphodiester links) and by the difference in chromatographic properties between the 3' phosphoryl product and (Tp)gT, elution time 17.3 min and 16.1 min, respectively. HPLC was carried out with a 4×250 mm Omni Pac® NA100 column, flow rate 1 ml/min, starting with 20% buffer B (1.5M NaCl in 10 mM NaOH) and 80% buffer A (10 mM NaOH) and increasing B at the rate 1%/min. The Tm value for dissociation of the complex formed between (Tp)$_{10}$ and poly(dA) was 21.0° C. (0.1M NaCl), slightly less than that for the complex formed between (Tp)gT and poly(dA) (22.0° C.).

We have also employed this procedure successfully to immobilize nucleoside phosphoramidates on aminopolystyrene and NH$_2$Tenta Gel® (RAPP Polymer Inc., Germany) supports and to synthesize oligonucleotides with mixed base sequences. It therefore appears promising for a wide range of applications.

An application of the above is the synthesis of oligonucleotides immobilized on an insoluable support. Since the link of

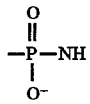

is stable to concentrated ammonium hydroxide, protecting groups can be removed without cleaving the oligonucleotides from the support. Such oligomers could be useful as probes and in constructing affinity columns.

In preparing the exemplary compounds set forth in Tables 1 and 2, addition of monomer units was carried out on a Cyclone Milligen/Biosearch synthesizer. The manual syringe technique was used for addition of dimer blocks. The starting points for the syntheses were: dt-succinyl-LCAA CPG for 1–5, 14,15; III for 11–13; and VIIIb for the precursors of 17 and 19; and VIIIc (same as VIIIb but with β-cyanoethyl in place of methyl) for the oligomer phosphoramidate precursors for 21, 23, and 24. The support contained approximately 0.5 µmole of the terminal nucleoside in each case. Standard phosphoramidite chemistry was used in coupling the monomeric dT units in preparing 1–5, 14–19, 22, 23 and in coupling the dimer blocks in preparing 14,15. H-Phosphonate chemistry was used for all couplings in preparing 11–13 and for the dimer blocks in 2–5 by modifying the method of B. C. Froehler et al.[20] by oxidizing with 0.2M iodine in pyridine/water 95/5 v/v for 25 minutes[21]. Oligomers in which methoxyphosphoramidate were to be retained were cleaved from the support with 5% ammonium hydroxide in methanol at room temperature, 0.5 hour (when an oxalyl anchor was used, i.e. for 11–13) or concentrated ammonium hydroxide, 55° C., 20 min (when a succinyl anchor was used, for 14–15). In cases where phosphoryl protecting groups (preparation of 6–10 and precursors of 18, 19) or base protecting groups (preparation of 22, 23) were to be removed, the solid supported oligomers were treated with concentrated ammonium hydroxide at 55° C. for 17 hours.

The methyl phosphonate derivatives (20 and precursors of 21, 24) were cleaved from the support by successive treatment with hydrazine/acetic acid/pyridine and ethylenediamine/ethanol as described by P. S. Miller, (1991) in "Oligonucleotides and Analogues: A Practical Approach," F. Eckstein, Ed. Oxford University Press, 137–154. This treatment also removed the β-cyanoethyl protecting group at the phosphoramidate linkage. After filtration and concentration, the oligonucleotides were isolated by ion exchange chromatography and further purified by reversed phase chromatography. The precursors to the 3'-aminooligonucleotides all terminated with the group: ... nucleoside-NHP(O)(O$^-$)O-thymidine. In each case, the oligomer with a terminal 3'-amino group was generated by cleaving the phosphoramidate link by treatment with 80% aqueous acetic acid for 18–20 h at room temperature; then the oligomer was isolated by RP chromatography. In confirmation of the presence of an amino group, the cleavage products gave a positive ninhydrin test. The retention times for RP chromatography for precursor (Tm)$_9$ T-NHP(O)(O$^-$)O-T, compound 21, precursor d(TmAmTmTmCmAmGmTmCmAmT-NHP(O)(O$^-$)O-T), compound 24, precursor d(DMT-TATTCAGTCATNHP(O)(O$^-$)O-T), and compound 23 are: 28.5, 30.4; 26.5, 28.4; 31.4, and 17.5 minutes, respectively.

Following is a summary of general methodology and reagents employed. The methyl and cyanoethyl phosphoramidates of 5'-DMTr-dt and DMTr-dT-LCAA CPG, 500 Å were purchased from commercially available sources.

Ion exchange (IE) and reversed phase (RP) HPLC analyses were performed on a Dionex chromatograph. For IE analysis, a Dionex OmniPac NA100, 4×250 mm column was used, with a 1%/min or 2%/min gradient of 1.0M NaCl in 0.03M TEAA buffer, pH 7.0; flow rate, 1.0 ml/min. RP chromatography was carried out on a Hypersil ODS 5µ, 4.6×200 mm column from Hewlett Packard, with a 1%/min gradient of acetonitrile in 0.03M TEAA buffer, pH 7.0; flow rate, 1 ml/min.

Column chromatograph was performed on Kieselgel 60, 70–230 mesh ASTM from Merck, with a 0–10% gradient of methanol in dichloromethane that contained triethylamine, 1% v/v. DC-Fertigplatten SIL G-25 $^{UV}$254 precoated plates from Macherey-Nagel were used for TLC analysis. The plates were eluted with dichloromethane/ethanol/triethylamine 89/10/1 v/v/v (solvent a), or dichloromethane/ethanol 85/15 v/v (solvent b), or i-propyl alcohol/ammonium hydroxide/water 7/1/2,v/v/v (solvent c).

NMR spectra were recorded on a Varian XL-400 spectrometer at 162 MH$_z$ for $^{31}$p spectra, with 85% phosphoric acid in D$_2$ as an external standard, and at 400 MH$_z$ for $1_H$ spectra, with TMS as external standard. The thermal dissociation data were collected on a Perkin Elmer Coleman 570 spectrophotometer equipped with a Pelletier temperature controller.

The various formulas and reaction schemes referred to below are set forth in the Formula Chart A and in Chart B, Chart C, and Chart D hereof.

Preparation of Dimer I and IV (Solution Phase)

Compound IV (see Chart B) was prepared in solution and converted to the hydrogen phosphonate Compound I (See Formula Chart A) as described by S. Gryaznov et al.[16]. The properties for compound IV are:

$^{31}$P NMR (in pyridine-d$_5$), δ 9.43, 938; RP HPLC elution time, 49.0, 50.0 min (stereoisomers at P); TLC (solvent a) Rf 0.25. Spectral data for Compound I are: $^{31}$P NMR (pyridine-d$_5$, δ 9.42 ppm (phosphoramidate), δ 4.22 and –0.84 ppm (H-phosphonate group, $^J$p-H 613.1 Hz).

Preparation of III and Dimer IV (Solid Support Reaction)

To prepare the bound nucleoside represented by II in Chart B, 5'-N-Monomethoxytrityl-5'-amino-5'-deoxythymidine prepared as described by W. Bannwarth[7] was loaded (~40 μmold/g support) on LCAA-CPG via an oxalyl anchor by the procedure used for loading 5'-O-Dimethoxytritylthymidine[23], and a sample (40 μmold/g support) of the solid containing 1.5 μmole of 5'-$NH_2$dT was placed in a syringe for synthesis. Solutions were drawn in and then expelled from the syringe in successive steps in the synthetic sequence as follows: (a) 3% dichloroacetic acid (DCA) in dichloromethane, 1.5 min; (b) acetonitrile wash; (c) methyl N,N-diisopropylphosphoramidite of 5'O-dimethoxytritylthymidine (100 μl of 0.1M solution in acetonitrile) and tetrazole (100 μl of 0.4M solution in acetonitrile), 3 min; (d) acetonitrile wash; (e) 0.1M iodine in pyridine/tetrahydrofuran/water 47/47/6, 1 min; (f) dichloromethane wash followed by methanol wash; to give the bound dimer III (Chart B). To obtain dimer IV, bound dimer III in treated with 5% ammonium hydroxide in methanol followed by rapid stripping of the ammonia/methanol solution.

Preparation of Dimer IX (Solution Phase)

Chloro (diisopropylamino) methoxyphosphine (0.44 ml, 2.3 mmole) was added over a period of 5 min with vigorous stirring to a solution of 3'-O-levulinylthymidine compound VIa (0.68 g, 1.8 mmole) in dry dichloromethane (20 ml) and diisopropylethylamine (0.5 ml). Compound VIa was prepared as described by A. Hassner et al.[24]. After 15 min, tetrazole (10 ml of a 0.4M solution in 10% aqueous acetonitrile) was added and the mixture was stirred an additional 15 min. The mixture was diluted with dichloromethane (50 ml) and washed with saturated aqueous sodium chloride (3×25 ml) and water (25 ml). The organic layer was collected, dried (sodium sulfate), and concentrated in vacuo. The resulting foam was dried under reduced pressure in a desiccator over phosphorus pentoxide for 16 hours to give compound VIIa. Compound VIIa was taken up in anhydrous acetonitrile (6 ml) and treated with 5'-O-trityl-3'-amino-3'-deoxythymidine (270 mg, 0.56 mmole)[25] in carbon tetrachloride (6 ml) and triethylamine (1 mi). Within 20 min, as judged by TLC analysis, all of the tritylaminonucleoside (solvent b, Rf 0.35) had been converted to the dimer (VIIIa) (solvent b, Rf 0.65). The solvent was then evaporated under reduced pressure and the residue was treated with 5 ml of a 0.5M solution of hydrazine hydrate in pyridine/acetic acid, 4/1, v/v, to remove the levulinyl groups. Analysis by TLC showed complete transformation of VIIIa within 20 min to Compound IX Rf 0.15. The reaction mixture was diluted with dichloromethane (100 ml), washed with saturated aqueous sodium chloride and water, dried over sodium sulfate, and concentrated in vacuo. Chromatography on silica gel afforded dimer IX, 400 mg (92% based on the aminonucleoside): TLC (solvent b) Rf 0.50; RP HPLC, elution time 47.5 min; $^{31}$P NMR δ 8.28 8.63 ppm; FAB mass spectrum, M+H$^+$ 802, M+Na$^+$ 824.

Preparation of Dimer Phosphoramidite, X (Solution Phase)

Compound IX was phosphitilated and transformed to dimer X according to the procedure in the A. Barone et al. reference[18] for preparing nucleoside phosphoramidites. It was precipitated from pentane and used for oligonucleotide synthesis without additional purification. The purity, estimated by RP HPLC analysis was 96%. Four bands appear in the $^{31}$p NMR spectrum (pyridine-$d_5$, undercoupled): δ 146.00, 146.49 ppm (phosphoramidite stereoisomers), δ 9.07 k, 8.56 ppm (phosphoramidate stereoisomers) see FIG. 3). The isomers separated as two peaks on analytical RP HPLC (RP HPLC elution time, 62.5 and 63.5 min) and appeared as one spot on TLC (Rf 0.70, solvent a).

Solid Phase Synthesis of Dimer XI

The reactions were carried out at room temperature with the solid supported reactants in a syringe, starting with dT-succinyl-LCAA-CPG (VIb) (45 mg, 1.5 mmole of dT). The successive treatments were: (a) 0.5 ml of 0.2M chloro (diisopropylamino)methoxyphosphine in dichloromethane/diisopropylethylamine 9/1 v/v, 10 min; (b) acetonitrile wash (3×0.5 ml); (c) 1 ml of 0.4M tetrazole in acetonitrile/water 5/1 v/v, 5 min; (d) acetonitrile wash (5×0.5 ml) to give compounds VIIb which is treated as follows: (e) 0.55 ml of 0.2M 5'trityl-3'-amino-3'-deoxythymidine[25] in acetonitrile/carbon tetrachloride/triethylamine 5/5/1 v/v/v, 1.5 h; (f) acetonitrile wash (5×0.5 ml) and dichloromethane wash (3×0.5 ml); to give compound VIIIb which is detrilylated by treatment with 3% dichloroacetic acid in dichloromethane for 30 min. Treatment of the detrilylated compound with concentrated ammonium hydroxide (20 min. 55° C.), concentration of the ammonia solution, and RP HPLC gave dimer XI as 96% of the nucleotide material eluting from the column. This product was identical in properties to XI obtained by mild acid hydrolysis of X prepared in solution.

Labelling with Fluorescein

A solution of fluorescein isothiocyanate (Aldrich) 10 μl of 10% solution in DMF) was added to the aminooligonucleotide (0.25 $A_{260}$ units) in 0.2M borate buffer, pH 8.6, 100 μl). The mixture was shaken in the dark overnight; then water (400 μl) was added and the mixture was desalted by gel filtration on a NAP-5 column (Pharmacia). The filtrate (1 ml) was collected, concentrated, and repurified by gel filtration. Reversed phase HPLC showed that the oligomers were converted essentially completely to the fluorescein conjugated derivatives: for the derivative of 3'-amino-oligomer 18, elution time 21.5 min (compared to 19.0 min for the starting amino-oligomer); for the derivative of 5',3'-diamino-oligomer 19, elution time 23.6 min (compared to 18.5 min for the starting diaminooligomer). The UV spectra show the presence of both the thymidine and fluorescein moieties: for derivative of 18, $\lambda$max $^{266, 456, 480\ nm}$, $\lambda$min $^{240, 332, 468\ nm}$; for derivative of 19, $\lambda$max $^{266, 460, 482}$, $\lambda$min $^{250, 332, 470\ nm}$.

Stepwise Hydrolysis of Dimers

On treatment with 0.8% trifluoroacetic acid in dichloromethane (40 min, room temp), dimer IX (positive trityl test with trifluoroacetic acid vapor) was converted essentially quantitatively to a single nucleotide product lacking the trityl group corresponding to dimer XI; TLC (solvent b) RF 0.17, RP HPLC elution time 18.8 min. When warmed with ammonium hydroxide (16 h, 55° C.) dimer XI gave the corresponding phosphoramidate salt, dimer XII (~99%); TLC (solvent b) Rf 0.05; RP HPLC elution time 14.0 min; $^{31}$P NMR, δ 7.75 ppm (single peak); $^{1}$H NMR in $D_2O$ (δ in ppm): 1.83 (s, 6 H, Me), 2.33, 2.43 (m, 4 H, H2',2"), 3.60 (m, 1 H, —NH—P), 3.81, 3.92 (m, 4 H, 5', H5"), 4.06 (m, 2 H, H4'), 4.75 (m, 1 H, H3'), 5.92 (m, 1 H, H1'), 6.29 (t, 1 H, H1'), 7.82 (s, 1 H, H6), 7.85 (s, 1 H, H6). The phosphoramidate salt hydrolyzed cleanly to 3'-aminodeoxythymidine, Compound XII, RP HPLC 9.0 min, positive ninhydrin test) and thymidine 5'-phosphate Compound XIV (RP HPLC 6.7 min) when treated with 80% aqueous acetic acid (16 h, room temp). Compounds XIII and XIV co-eluted with standard samples of 3'-amino-3'-deoxythymidine and thymidine 5'phosphate and differed from 5'-amino-5'-deoxythymidine (RP HPLC 6.2 min) and thymidine 3'-phosphate (RP HPLC 7.4 min).

A similar series of reactions with Compound IV afforded the related family of hydrolytic products except de-dimethoxytritylation was affected with 80% aqueous acetic acid. Compound IV was treated with 80% aq. acetic acid for 0.5 h, to give V, TLC (solvent a) RF 0.10, RP HPLC elution time 21.5 and 22.1 min (stereoisomers), $^{31}$p NMR (pyridine-$d_5$) 9.43, 9.38 ppm (stereoisomers). Compound V was treated with ammonium hydroxide for 16 h at 55° C. to give the anionic phosphoramidate produced by demethylation, Compound XV (Chart D), TLC (solvent c) Rf 0.6, RP HPLC elution time 15.2 min, $^{31}$p NMR (D$_2$O) δ 8.73 ppm. Treatment of Compound XV with 80% aq. acetic acid for 16 h at room temperature gave 5'-amino-5'-deoxythymidine, Compound XVI, and thymidine 3'-phosphate, Compound XVII.

For enzymatic hydrolysis of 18, 0.2 A$_{260}$ units of oligonucleotide, 8 U of phosphomonoesterase and 0.22 U of phosphodiesterase from Crotalus durissus (Boehringer Mannheim) were incubated for 3 h and then overnight in 100 μl of 10 mM Tris•HCl and 10 mM MgCl$_2$.

Effects of Modifications on Hybridization

Thermal dissociation (Tm) values for complexes formed between poly (dA) and decamers containing one to three internucleoside phosphoramidate links are presented in Table 1. The following conclusions may be drawn from these results. (i) Introduction of a single 3'-OP(O)(O$^-$)NH-5' link in the backbone of an oligomer has little effect on the hybridization properties, even at the ten-mer level (the Tm values for 2, 3, 4, 6 are ±°C. that for the parent unmodified complex, 1). This result indicates that such links may be used to join sizeable oligonucleotide blocks without compromising the hybridization properties of the product. (ii) Introduction of two or more phosphoramidate links separated by a few nucleotides leads to destabilization (compare 5 with 2–4, 8 with 6,7, and 10 and 9). This result suggests that although a single modified site may have little influence on the observed binding, it induces some change in geometry that can be transmitted through several nucleotide units in the double helix. (iii) Introduction of a phosphoramidate with the reverse orientation, 3'-NHP(O)(O$^-$)O-5', leads to enhancement in stability of the heteroduplex (~6° C. increase for the doubly modified oligomer, 9, relative to the parent, 1). (iv) Oligomers containing the corresponding methyl ester phosphoramidate links (11–15) bind well to poly(dA), even when up to a third of the internucleoside links are modified. For phosphoramidate modification with the 3'-O-5'-N orientation, the Tm values for the methyl ester derivatives higher than the values for the corresponding anionic modifications (compare 11–13 with 6–8). The reverse relationship holds for the phosphoramidates with the 3'N-5'O orientation.

Data for complexes formed between the amino terminal oligonucleotides (17–19) and d(AAAAAAAAAA), poly (dA), and poly(A) are presented in Table 2, and representative plots of normalized absorbance versus temperature are shown in FIG. 5. A striking result is the enhancement in Tm values associated with substitution of NH$_2$ for OH at an end of a thyidylate oligomer. The greatest effect was found for the 3'-amino derivative. In connection with potential applications as inhibitors of gene expression, it is significant that enhancement was observed with the ribo as well as deoxyribo complementary strands. Binding of the 3'-amino thymidylate oligomers was not further enhanced by presence of a 5'-amino group (compare 18 and 19). This property may reflect electrostatic repulsion of the terminal 3' and 5' —NH$_3^+$ groups in molecules of 19 aligned along a homonucleotide complement.

The large effect of the 3'-amino group on the stability of complexes involving the thymidylate oligomers suggests that this modification could prove beneficial in enhancing hybridization of oligomers used as diagnostic tools and antisense agents. As a test of the generality of the effect, we have prepared and examined the methyl phosphonate and mixed-base oligomers shown in Table 3 (compounds 20–24). Indeed, we find that a terminal 3'-amino group leads to significant enhancement in Tm in both systems (11° C. for methyl phosphonate 21 relative to 20; 10° C. for the mixed base phosphodiester eleven-mer 23 relative to 22). It may be noted that the Tm value for the 3'-amino mixed-base methylphosphonate derivative (24) is higher than that for the corresponding unmodified phosphodiester oligomer.

The modified compounds in Tables 1–3 contain units derived from either 3'-amino-3'-deoxythymidine or 5'-amino-5'-deoxythymidine. It is interesting that both for the phosphoramidate and for the terminal amino derivates the enhancement in stability of the heteroduplexes is greater for compounds derived from the 3'-aminonucleoside. This property may reflect a favorable conformational change in the sugar-phosphate backbone that stems from the replacement of oxygen by nitrogen.

The invention has been described in an illustrative manner, and it is to be understood the terminology used is intended to be in the nature of description rather than of limitation.

Obviously many modifications and variations of the present invention are possible in light of the above teachings. Therefore, it is to be understood that within the scope of the appended claims the invention may be practiced otherwise than as specifically described.

TABLE 1

Thermal Dissociation of Complexes of Decamers with Internal Phosphoramidate Links (pH 7.05, 15 mM phosphate buffer, 100 mM NaCl)

| Oligomer | Tm °C.[a] | | Oligomer | Tm °C. |
|---|---|---|---|---|
| 1. TTTTTTTTTT | 22 | | | |
| 2. TTTTTTTTpnTT | 21 | | | |
| 3. TTTTTpnTTTTT | 23 | | | |
| 4. TpnTTTTTTTTT | 21.5 | | | |
| 5. TTTTpnTTpnTTpnTT | 10 | | | |
| 6. TTTTTTTTTpnT | 22.5 | 11. | TTTTTTTTTp(ome)nT | 25 |
| 7. TpnTTTTTTTTpnT | 20 | 12. | Tp(ome)nTTTTTTTTTp(ome)nT | 23.5 |
| 8. TpnTTTTpnTTTTpnT | 13 | 13. | Tp(ome)nTTTTp(ome)nTTTTp(ome)nT | 20.5 |
| 9. TnpTTTTTTTnpTT | 28.5 | 14. | Tnp(ome)TTTTTTTnp(ome)TT | 25.5 |
| 10. TTTTnpTTnpTTnpTT | 23 | 15. | TTTTnp(ome)TTnp(ome)TTnp(ome)TT | 21.5 |

[a]Equimolar amounts of dT and dA or A residues; total nucleotide concentration, ~1 A$_{260}$ unit/ml; pH 7.05 (15 mM phosphate buffer). Solutions were equilibrated at 0° C. and the temperature increased stepwise in increments of 3° C. every 5 min.

TABLE 2

Thermal Dissociation of Complexes of Decamers with Terminal Amino Groups (Tm values, °C.)[a]

| Oligomer | d-AAAAAAAAAA [NaCl] | | Poly(dA) [NaCl] | | Poly(A) [NaCl] |
|---|---|---|---|---|---|
| | 23 mM | 100 mM | 23 mM | 100 mM | 100 mM |
| 16. TTTTTTTTTT | 5.5 | 17.5 | 6.5 | 22 | 18 |
| 17. (NH$_2$)TTTTTTTTTT | 8.5 | 20.5 | 13 | 27.5 | 22 |
| 18. TTTTTTTTTT(NH$_2$) | 11.5 | 23.5 | 15 | 31 | 25 |
| 19. (NH$_2$)TTTTTTTTTT(NH$_2$) | 11.5 | 22.5 | 13.5 | 29 | 24 | a. The Tm measurements were carried as described in Table 1.

FORMULA CHART A

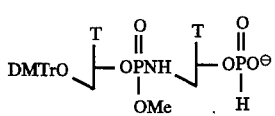

I

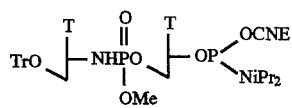

X

CHART B
(Scheme 1)

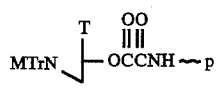

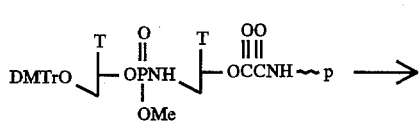

III

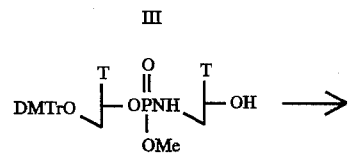

IV

-continued
CHART B
(Scheme 1)

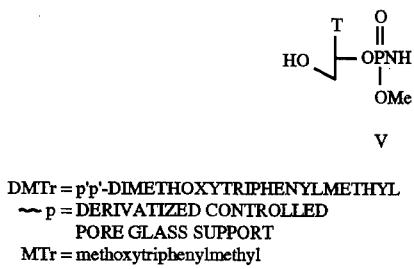

V

DMTr = p'p'-DIMETHOXYTRIPHENYLMETHYL
~p = DERIVATIZED CONTROLLED PORE GLASS SUPPORT
MTr = methoxytriphenylmethyl

CHART C
(Scheme 2)

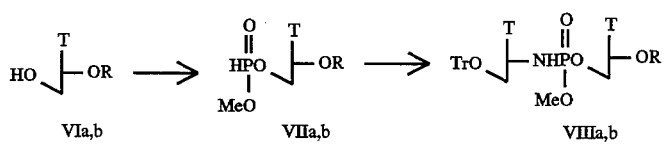

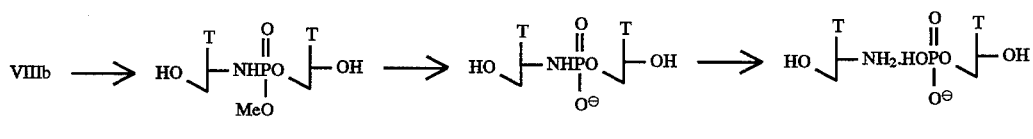

-continued
CHART C
(Scheme 2)

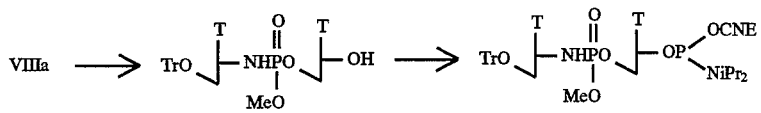

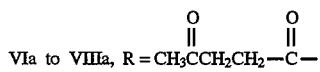

CHART D

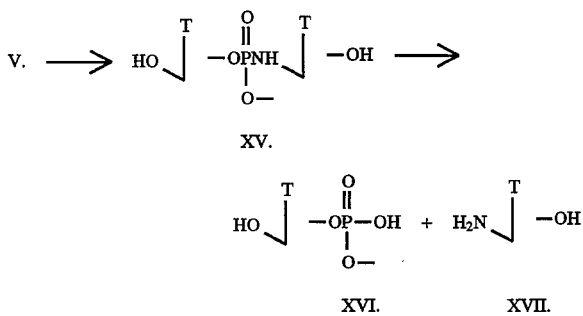

REFERENCES

1. Letsinger, R., et al., J. Org. Chem., 35:3800–3803 (1970)
2. Mungall, W., et al., J. Org. Chem., 40:1659–1662 (1975)
3. Green, G., et al., Nucleic Acids Res., 2:1123–1127 (1975)
4. Zielinski, W., et al., Nucleic Acids Res., 13:2469–2484 (1985)
5. Zielinski, W., et al., Nucleic Acids Res., 15:1699–1715 (1987)
6. Zielinski, W., et al., Nature, 327:346–347 (1987)
7. Bannwarth, W., Helv. Chem. Acta, 71:1517–1527 (1988)
8. Gromova, E., et al., Mol. Biol., 20:29–40 (1986)
9. Sokolova, N., et al., FEBS Letters, 232:153–155 (1988)
10. Dolinnaya, N., et al., Nucleic Acids Research, 16:3721–3738 (1988)
11. Shabarova, Z., Biochem., 70:1323–1334 (1988)
12. Sproat, B., et al., Nucleic Acids Res., 15:6181–6196 (1987)
13. Letsinger, R., et al., J. Am. Chem. Soc., 94:292–293 (1972)
14. Letsinger, R., et al., Biochemistry, 15:2810–2816 (1976)
15. Letsinger, R., et al., Nucleic Acids Res., 3:1053–1063 (1976)
16. Gryaznov, S., et al., Tetrahedron Lett., 31:3205–3208 (1990)
17. Atherton, F., et al., J. Chem. Soc., 660–663 (1945)
18. Barone, A., et al., Nucleic Acids Res., 12:4051–4061 (1984)
19. Agrawal, S., et al., Proc. Nat'l. Acad. Sci., 85:7079–7083 (1988)
20. Froehler, B., et al., Tetrahedron Lett., 27:469–472 (1986)
21. Garegg, P., et al., J. Chem. Soc. Perkin Trans. I, 1269–1273 (1987)
22. Miller, P., "Oligonucleotides and Analogues: A Practical Approach," F. Eckstein, Ed., Oxford Univ. Press, 137–154.
23. Alul, R., et al., Nucleic Acids Res., 19:1527–1532 (1991)
24. Hassner, A., et al., J. Am. Chem. Soc., 97:1614–1615 (1975)
25. Glinski, R., et al., J. Chem. Soc. Chem Comm., 915–916 (1970)

We claim:

1. An oligodeoxyribonucleotide consisting of nucleosides wherein the base is selected from adenine, thymine, cytosine, guanine, and uracil and at least one internucleoside link having the structure

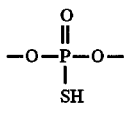

and at least one internucleoside link having the structure

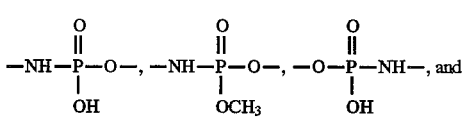

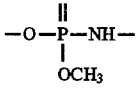

and wherein the remainder of the internucleoside links are phosphodiester links.

* * * * *